United States Patent
Hell et al.

(10) Patent No.: US 7,858,826 B2
(45) Date of Patent: Dec. 28, 2010

(54) PROCESS FOR PRODUCING 6-DIMETHYLAMINOMETHYL-PHENYL-CYCLOHEXANE-1,3-DIOLS

(75) Inventors: Wolfgang Hell, Aachen (DE); Oswald Zimmer, Wuerselen (DE); Markus Kegel, Moenchengladbach (DE); Olaf Schaefer, Stolberg (DE); Felix Spindler, Starrkirch-Wil (CH); Anita Schnyder, Hersberg (CH); Urs Siegrist, Frick (CH); Detlef Heller, Rostock (DE); Hans-Joachim Drexler, Gross Schwass (DE)

(73) Assignee: Gruenenthal GmbH, Aachen (DE)

( * ) Notice: Subject to any disclaimer, the term of this patent is extended or adjusted under 35 U.S.C. 154(b) by 53 days.

(21) Appl. No.: 12/394,727

(22) Filed: Feb. 27, 2009

(65) Prior Publication Data

US 2009/0227813 A1    Sep. 10, 2009

(30) Foreign Application Priority Data

Feb. 29, 2008    (EP)    ................... 08003846

(51) Int. Cl.
*C07C 215/42*    (2006.01)
(52) U.S. Cl. ...................................... 564/443; 564/305
(58) Field of Classification Search ....................... None
See application file for complete search history.

(56) References Cited

U.S. PATENT DOCUMENTS 5,733,936 A    3/1998    Buschmann et al.

FOREIGN PATENT DOCUMENTS

EP    0 753 506 B1    1/1997

*Primary Examiner*—Brian J Davis
(74) *Attorney, Agent, or Firm*—Crowell & Moring LLP

(57) ABSTRACT

A process for producing 6-dimethylaminomethyl-1-(3-hydroxy- or 3-$C_1$-$C_4$ alkoxyphenyl)-cyclohexane-1,3-diols from 6-dimethylaminomethyl-1-hydroxy-1-(3-hydroxy- or 3-$C_1$-$C_4$ alkoxyphenyl)-cyclohexane-3-ones by catalytic hydrogenation in the presence of heterogeneous or homogeneous catalysts, or by using metal hydrides.

20 Claims, No Drawings

PROCESS FOR PRODUCING 6-DIMETHYLAMINOMETHYL-PHENYL-CYCLOHEXANE-1,3-DIOLS

BACKGROUND OF THE INVENTION

The present invention relates to a process for producing 6-dimethylaminomethyl-1-(3-hydroxy- or 3-$C_1$-$C_4$ alkoxyphenyl)-cyclohexane-1,3-diols from 6-dimethylaminomethyl-1-hydroxy-1-(3-hydroxy- or 3-$C_1$-$C_4$ alkoxyphenyl)-cyclohexane-3-ones by catalytic hydrogenation in the presence of heterogeneous or homogeneous catalysts, or by using metal hydrides.

U.S. Pat. No. 5,733,936 (=EP 753,506) discloses 6-dimethylaminomethyl-1-(3-hydroxy- or 3-$C_1$-$C_4$ alkoxyphenyl)-cyclohexane-1,3-diols which are effective analgesics, suitable in particular for the treatment of intense pain. These compounds have 3 asymmetric carbon atoms. The 6-dimethylaminomethyl-1-(3-hydroxy- or 3-$C_1$-$C_4$ alkoxyphenyl)-cyclohexane-1,3-diols are obtained by hydrogenating corresponding racemic 3-cyclohexanones with metal hydrides, such as sodium borohydride (Example 18) or diisobutylaluminium hydride (Example 20), and separation of the racemates thus formed by means of HPLC on chiral columns then yields the 1R,3R,6R and 1S,3S,6S stereoisomers. This method of production of enantiomer-pure compounds is not particularly advantageous for industrial applications. It is also known that both the aforementioned cyclohexane-1,3-diols and the starting materials (3-cyclohexanones) decompose slightly, or rather tend to undergo elimination reactions with the formation of unsaturated compounds. Owing to this sensitivity of the compounds, the formation of undesirable by-products during hydrogenation may be so high, or even predominate (such as when reducing with diisobutylaluminium hydride), that these reactions are not particularly economical and are thus less suitable for the industrial production of pharmaceutical active ingredients.

It has been found that some stereoisomers are characterized by particularly good efficacy. These stereoisomers are 1R,3R,6R and 1S,3S,6S stereoisomers of formulas III and IV or mixtures thereof

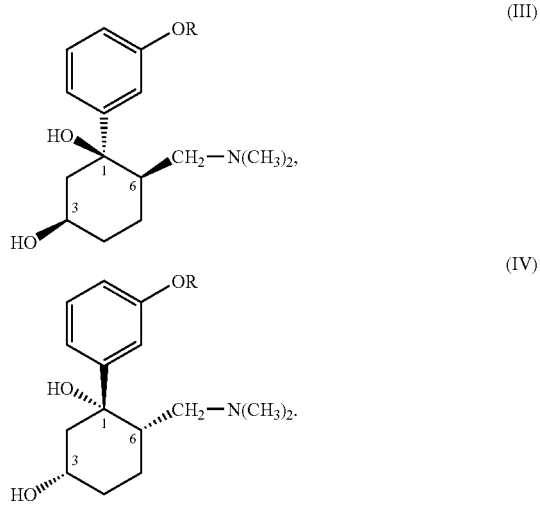

The 1R,3S,6R and 1S,3R,6S stereoisomers of formulas V and VI

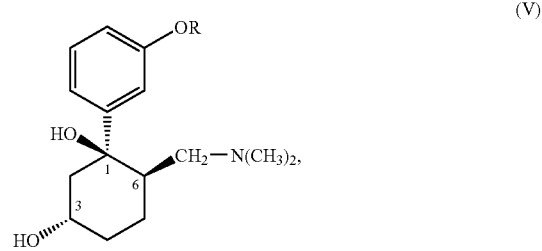

are, in contrast, less desirable and their formation should thus be avoided as far as possible during production.

SUMMARY OF THE INVENTION

It was accordingly an object of the present invention to provide a process for the targeted production of stereoisomers of formulas III and IV or mixtures thereof, in which the formation of undesirable by-products or decomposition products is avoided as far as possible.

Surprisingly, it has been found that the targeted production of stereoisomers of formulas III and IV or mixtures thereof is possible and that, with good to high conversion rates and yields, it is possible to obtain outstanding selectivity and purity if the keto group of 1R,6R- or 1S,6S-6-dimethylaminomethyl-1-hydroxy-1-(3-hydroxy- or 3-$C_1$-$C_4$ alkoxyphenyl)-cyclohexane-3-one or mixtures thereof is hydrogenated in the presence of selected catalysts in the heterogeneous or homogeneous phase with hydrogen, or with alkali metal trialkyl borohydrides or alkali metal trialkyl aluminium hydrides. The formation of by-products can, surprisingly, be considerably reduced, for example to less than 10% by weight and even to less than 5% by weight in the reaction product. If a freshly prepared starting product is used, the amount of by-products can often be reduced to 3% by weight or less.

The invention thus relates to a process for producing compounds of formulas III or IV or mixtures thereof,

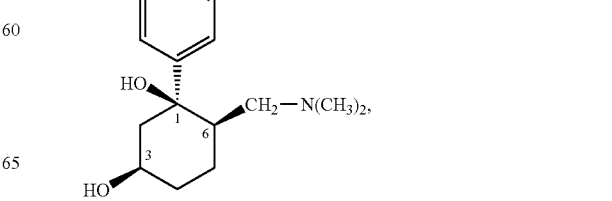

-continued

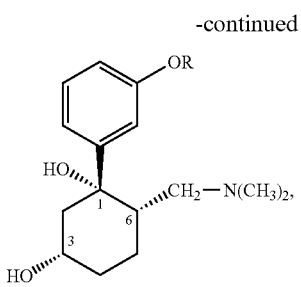
(IV)

where R represents hydrogen or $C_1$-$C_4$ alkyl, by hydrogenating the keto group of enantiomer-pure compounds of formulas I or II or mixtures thereof,

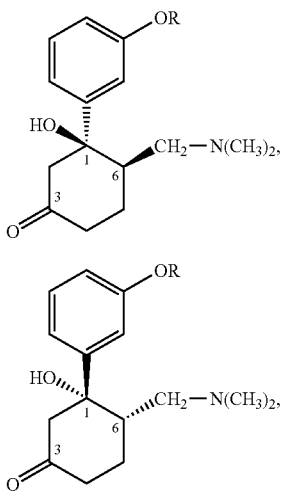

characterized in that hydrogenation is carried out
a) with hydrogen in the presence of platinum dioxide or Raney nickel in the heterogeneous phase;
b) with hydrogen in the presence of a rhodium, iridium or ruthenium complex with chiral diphospine ligands in the homogeneous phase; or
c) with an alkali metal trialkyl borohydride or an alkali metal trialkyl aluminium hydride.

When R is an alkyl it may, for example, be methyl, ethyl, n- and isopropyl, or n, iso, sec- and tert-butyl. In a preferred embodiment R represents hydrogen or, in particular, methyl. In a further preferred embodiment R is methyl.

In accordance with the process according to the invention, the diastereomers of formulas III and IV are obtained in a predominantly diastereomer-pure form, i.e., the ratio of diastereomers of formulas III and IV to diastereomers of formulas V and VI (also referred to as selectivity hereinafter) is, for example, at least 75:25, preferably at least 80:20, more preferably at least 85:15 and particularly preferably at least 90:10. Depending on the selection of catalysts and reaction conditions, a ratio of at least 95:5 and higher may be obtained with heterogeneous and homogeneous catalysts. Reaction with alkali metal trialkyl borohydrides or alkali metal trialkyl aluminium hydrides even leads to ratios of at least 99:1.

The process according to the invention may be performed, in particular, at normal pressure or at overpressure. Better selectivities are often observed at normal pressure and low overpressue. In variations a) and b) of the process, the hydrogen pressure may be, for example, from $10^5$ to $2\times10^7$ Pa (Pascal). With variation a) of the process, a hydrogen pressure of preferably from $10^5$ to $10^7$ Pa, preferably from $10^5$ to $5\times10^6$ Pa is used, and with variation b) of the process a hydrogen pressure of from $10^5$ to $10^7$ Pa, preferably from $10^6$ to $10^7$ Pa is used. The process according to the invention may be carried out at low or high temperatures, for example temperatures of from −80 to 150° C., preferably from −20 to 100° C., and particularly preferably from −20 to 80° C. The optical purities are generally better at lower temperatures than at higher temperatures. In contrast, the reaction rates are slower and conversion rates reduced at lower temperatures. Variation c) of the process is advantageously carried out at temperatures of from −100° C. to 20° C., preferably at temperatures of from −90° C. to 10° C. and more preferably at temperatures of from −80 to 0° C.

Platinum dioxide, a commercially available catalyst, is preferably used in an amount of from 0.1 to 15% by weight, particularly preferably from 0.5 to 12.5% by weight and most particularly preferably from 1 to 10% by weight, based on the amount of compounds of formulas I and II. Raney nickel, which is another commercially available catalyst, is preferably used in an amount of from 1 to 50% by weight, particularly preferably from 3 to 50% by weight and most particularly preferably from 5 to 40% by weight, based on the amount of compounds of formulas I and II. Rhodium, iridium or ruthenium complexes with chiral diphosphines are preferably used in an amount of from 0.0001 to 10% by weight, particularly preferably from 0.001 to 5% by weight and most particularly preferably from 0.01 to 3% by weight, based on the amount of compounds of formulas I and II. Alkali metal trialkyl borohydrides and alkali metal trialkyl aluminium hydrides are generally used in equivalent amounts or in a small surplus of, for example, up to 0.5 equivalent or in a deficit of up to 0.2 equivalent, based on the amount of compounds of formulas I and II. Heterogeneous catalysts may be recycled, it being possible to compensate for losses in activity by partial replacement with a fresh catalyst.

The process according to the invention and, optionally, in situ production of homogeneous catalysts may be carried out either in the presence of a preferably inert solvent (reaction medium) or not, it being possible to use a solvent or a mixture of two or more, for example two or three, solvents. Suitable solvents are, for example, aliphatic, cycloaliphatic and aromatic hydrocarbons (for example pentane, hexane, petroleum ether, cyclohexane, methylcyclohexane, benzene, toluene, xylene), aliphatic halogen hydrocarbons (for example methylene chloride, chloroform, dichloroethane and tetrachloroethane), nitriles (for example acetonitrile, propanonitrile, benzonitrile), ethers (for example diethyl ether, diisopropyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), carboxylic acid esters and lactones (for example ethyl or methyl acetate, valerolactone), N-substituted lactams (for example N-methylpyrrolidone), carboxylic acid amides (for example dimethylformamide, dimethylacetamide), acyclic ureas (for example dimethylimidazoline), sulfoxides and sulfones (for example dimethyl sulfoxide, dimethyl sulfone, tetramethylene sulfoxide, tetramethylene sulfone), alcohols (for example methanol, ethanol, propanol, butanol, ethylene glycol monomethyl ether, ethylene glycol monoethyl ether, diethylene glycol monomethyl ether) and water. The solvents may be used alone or in a mixture of at least two solvents. Basic solvents are less preferred, since they may promote the formation of by-products.

When using platinum dioxide, additives such as glacial acetic acid or metal halides (for example $MgCl_2$) may preferably be used in an amount of, for example, from 0.5 to 1.5 equivalent, based on the amount of compounds of formulas I and II. Hydrogenation with platinum dioxide is preferably carried out in alcohols (for example methanol, ethanol, propanol and butanol) or in acetic acid (for example glacial acetic acid) as a solvent.

Hydrogenation with Raney nickel is preferably carried out in alcohols (for example methanol, ethanol, propanol and butanol), carboxylic acid esters (for example ethyl acetate) or aromatic hydrocarbons (for example toluene, xylene) as a solvent.

The compounds of formulas I or II may be used in such an amount that solutions or suspensions are formed.

Metal complexes of rhodium, iridium and preferably ruthenium with diphosphine ligands, which may optionally be formed in situ, are suitable for the process according to the invention for hydrogenating compounds of formulas I and II with hydrogen using homogeneous catalysts.

Diphosphines and the like are examples of diphosphine ligands, as can be found, for example, in overviews, inter alia in a) H. Brunner, W. Zettlmeier, *Handbook of Enantioselective Catalysis*, VCH Weinheim, 1993, Vol. 2, page 3 et seq.; b) R. Noyori, et al. in *Catalytic Asymmetric Synthesis Second Edition* (I. Ojima, Ed.), Wiley-VCH, Weinheim, 2000, page 1 et seq.; c) E. N. Jacobsen, A. Pfaltz, H. Yamamoto (Eds.), *Comprehensive Asymmetric Catalysis Vol I-III*, Springer Berlin, 1999, and in references mentioned therein.

Generally chiral structures of the secondary phosphine-skeleton-secondary phosphine type are also possible. The two secondary phosphine groups are preferably bound to a skeleton in such a way that a 5 to 10-membered ring, and more preferably a 5 to 8-membered ring, is formed in the metal complex together with the metal atom. The two secondary phosphine groups are optionally bound terminally to the carbon atoms of a $C_2$-$C_8$, preferably a $C_2$-$C_6$, and particularly preferably a $C_2$-$C_4$ chain, in which carbon atoms of the chain may be replaced with O, S and NH heteroatoms and/or N—$C_1$-$C_4$ alkyl and may be the carbon chain part of a monocyclic or polycyclic ring. The skeleton may preferably contain from 2 to 30 atoms, more preferably from 2 to 20 carbon atoms and may optionally also contain heteroatoms, preferably 1, 2, 3 or 4 heteroatoms. The skeleton may also comprise atoms of the transition metal, for example iron. The heteroatoms may preferably be selected from the group consisting of O, S, NH and N—$C_1$-$C_4$ alkyl. The skeleton may be unsubstituted or substituted once or more, for example 1, 2, 3, 4, 5 or 6 times, for example with substituents selected, independently of one another, from the group consisting of $C_1$-$C_6$ alkyl, $C_1$-$C_6$ alkoxy, $C_1$-$C_6$ alkylthio, $C_4$-$C_8$ cycloalkyl, phenyl, benzyl, phenoxy, benzyloxy, phenylthio, benzylthio, halogen (preferably F, Cl, Br), OH, tri ($C_1$-$C_6$ alkyl)silyl, secondary amino, —$CO_2H$, —$SO_3H$, —$CO_2R'$, —$SO_3R'$, —O—C(O)—R', —NH—C(O)R', —O—$SO_3$—R', and —NH—$SO_3R'$, in which R' represents $C_1$-$C_6$ alkyl, $C_4$-$C_8$ cycloalkyl, phenyl or benzyl. The skeleton may, in particular, be bivalent radicals of alkanes, heteroalkanes, alkenes, cycloalkanes, cycloalkenes, heterocycloalkanes, heterocycloalkenes, bicycloalkanes, bicycloheteroalkanes, spirobiscycloalkanes, spirobiscycloheteroalkanes, arylenes, heteroarylenes, bisarylenes, bisheteroarylenes or metallocenes, such as ferrocenes, it being possible to bond one or both phosphine groups to the cyclopentadienyl ring of a metallocene via a methylene, $C_1$-$C_{12}$ alkylidene, phenylene or —CR"R*-phenylene. R" and R* are, independently of one another, $C_1$-$C_6$ alkyl, $C_1$-$C_6$ alkoxy or phenyl, for example. The free bonds are at one or both cyclopentadienyl rings. In the case of cyclic skeletons, the free bonds are preferably at 1,2 positions and at the 6,6' position in 1,1'-bisaryls. Ligands which have C2 symmetry may preferably be used.

The secondary phosphine groups may also be bound via an oxygen atom to carbon atoms of the skeleton (in this case the skeleton is phosphinites).

A secondary phosphine group may be replaced by an oxazolinyl radical of formula

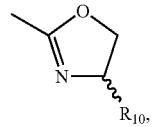

particularly in ferrocene skeletons, in which $R_{10}$ is $C_1$-$C_6$ alkyl, cyclohexyl, phenyl or benzyl.

The chirality of the diphosphine ligands may be based, in particular, on a planar isomerism (for example ferrocenes), atropisomerism, the presence of asymmetric carbon atoms and/or P atoms or any combination thereof.

Examples of skeletons of atropisomers are 1,1'-bisaryl und -bisheteroaryl (such as biphenyl, binaphthyl or bisthiophenyl) with secondary phosphine groups bound at the 2,2' positions and, optionally, further substituents, in particular at the 6 or 6,6' positions. Appropriate ligands are known to the person skilled in the art, for example by the trivial names Binap, Biphemp, Biphep and Solphos. Bicycloheptanes which are commercially available under the trivial name Bicp are also known to the person skilled in the art as a basic skeleton.

Examples of skeletons with planar chirality are those which are ferrocene-based with two secondary phosphine groups bound directly to each of the cyclopentadienyl rings or to a cyclopentadienyl ring at the 1,2 position and, optionally, chiral substituents at one or both cyclopentadienyl rings. Another example is ferrocenes, to which a secondary phosphine group and a further secondary phosphine group are bound at the 1,2 position of the cyclopentadienyl ring via an asymmetric carbon atom. A further example is ferrocenes, to which a secondary phosphine group is bound at the 1,2 position of the cyclopentadienyl ring via an asymmetric carbon atom and a second secondary phosphine group is bound via 1,2-phenylene. Examples of appropriate ligands are known to the person skilled in the art under the trivial names Josiphos, Walphos, Taniaphos, Mandyphos and Ferriphos.

Diphosphines with chiral P-rings which are particularly substituted in one or both a positions with a P atom are also known, for example phospholans and phosphetans. Secondary phosphine groups of this type may be bound at the 1,2 position of benzene, naphthalene, thiophene, benzothiophene, ethane and ferrocene. Examples of appropriate ligands are known to the person skilled in the art under the trivial names Rophos, Butiphane and Kephos.

Examples of skeletons with asymmetric carbon atoms are open chain skeletons with secondary phosphine groups bound at 1,2, 1, 3 or 1,4 positions, in particular aliphatic bicyclic ring systems with secondary phosphine groups bound at the 1,2 positions, or cyclic or heterocyclic five-membered rings with secondary phosphine groups bound at 3,4 positions, optionally via a methylene group. Five-membered rings with secondary phosphine groups bound at the 4 position and secondary phosphine methyl groups bound at the 2 position are also known. Trivial names for ligands of this type are Diop, Bppm, Bzppm, Depyphos, Norphos and Prophos.

Examples of diphosphines with chiral P atoms are 1,2-bis (secondary phosphine)ethanes with different substituents in the phosphine groups. A known example can be purchased under the trivial name Dipamp.

The secondary phosphine groups may contain the same or different hydrocarbon radicals as substituents, and the two secondary phosphine groups in the diphosphines may be the same or different. Good results can often be obtained if the secondary phosphine groups are different, rather than identical.

The hydrocarbon radicals may be unsubstituted or substituted once or more, for example 1, 2, 3, 4, 5 or 6 times and/or may contain, for example, 1, 2, 3 or 4 heteroatoms selected independently of one another from the group consisting of O, S, —N= and N($C_1$-$C_4$ alkyl). Preferably between 1 and 22, more preferably between 1 and 12 and particularly preferably between 1 and 8 carbon atoms may be contained.

A preferred secondary phosphine is one in which the phosphine group contains two radicals which are the same or different and are selected from the group of linear or branched $C_1$-$C_{12}$ alkyl; $C_5$-$C_{12}$ cycloalkyl or $C_5$-$C_{12}$ cycloalkyl-$CH_2$— which is unsubstituted or substituted with $C_1$-$C_6$ alkyl or $C_1$-$C_6$ alkoxy; phenyl, naphthyl, furyl or benzyl; or phenyl or benzyl substituted with halogen, $C_1$-$C_6$ alkyl, trifluoromethyl, $C_1$-$C_6$ alkoxy, trifluoromethoxy, $(C_6H_5)_3Si$, $(C_1$-$C_{12}$ alkyl$)_3Si$, or secondary amino.

Examples of p-substituents as an alkyl, which preferably contains from 1 to 6 carbon atoms, are methyl, ethyl, n-propyl, iso-propyl, n-butyl, iso-butyl, sec-butyl, tert-butyl, and the isomers of pentyl and hexyl. Examples of p-substituents as a cycloalkyl optionally substituted with alkyl are cyclopentyl, cyclohexyl, methyl and ethyl cyclohexyl and dimethyl cyclohexyl. Examples of p-substituents as phenyl and benzyl substituted with alkyl and alkoxy are methylphenyl, dimethylphenyl, trimethylphenyl, ethylphenyl, methylbenzyl, methoxyphenyl, dimethoxyphenyl, trimethoxyphenyl, trifluoromethylphenyl, bis-trifluoromethylphenyl, tris-trifluoromethylphenyl, trifluoromethylphenyl, bis-trifluoromethoxyphenyl, fluoro- and chlorophenyl and 3,5-dimethyl-4-methoxyphenyl.

Preferred secondary phosphine groups are those which contain radicals which are the same or different and are selected from the group of $C_1$-$C_6$ alkyl, cyclopentyl or cyclohexyl which is unsubstituted or substituted with from 1 to 3 $C_1$-$C_4$ alkyl or $C_1$-$C_4$ alkoxy, benzyl and, in particular, phenyl which are unsubstituted or substituted once or more with from 1 to 3 substituents selected independently of one another from the group consisting of $C_1$-$C_4$ alkyl, $C_1$-$C_4$ alkoxy, $C_1$-$C_4$-fluoroalkyl, $C_1$-$C_4$-fluoroalkoxy, F and Cl.

The secondary phosphino group preferably corresponds to the formula —$PR_1R_2$, in which $R_1$ and $R_2$ represent, independently of one another, a hydrocarbon radical having from 1 to 18 carbon atoms which is unsubstituted or substituted once or more, for example 1, 2, 3, 4, 5 or 6 times, with substituents selected independently of one another from the group consisting of $C_1$-$C_6$ alkyl, trifluoromethyl, $C_1$-$C_6$ alkoxy, trifluoromethoxy, $(C_1$-$C_4$ alkyl$)_2$amino, $(C_6H_5)_3Si$, $(C_1$-$C_{12}$ alkyl$)_3$Si and halogen, and optionally contains one or more, for example between 1 and 4, O heteroatoms.

$R_1$ and $R_2$ are preferably radicals selected from the group of linear or branched $C_1$-$C_6$ alkyl, cyclopentyl or cyclohexyl which is unsubstituted or substituted with from one to three $C_1$-$C_4$ alkyls or $C_1$-$C_4$ alkoxys, furyl, benzyl which is unsubstituted or substituted with from one to three $C_1$-$C_4$ alkyls or $C_1$-$C_4$ alkoxys and, in particular, phenyl which is unsubstituted or substituted with from one to three F, Cl, $C_1$-$C_4$ alkyls, $C_1$-$C_4$ alkoxys, $C_1$-$C_4$-fluoroalkyls or $C_1$-$C_4$-fluoroalkoxys.

$R_1$ and $R_2$ are particularly preferably radicals selected from the group $C_1$-$C_6$-alkyl, cyclopentyl, cyclohexyl, furyl and phenyl which is unsubstituted or substituted with from one to three F, Cl, $C_1$-$C_4$ alkyls, $C_1$-$C_4$ alkoxy and/or $C_1$-$C_4$-fluoroalkyl.

When $R_1$ and $R_2$ are different in the group —$PR_1R_2$, ligands are formed which are also P-chiral.

The secondary phosphine group may be a cyclic secondary phosphino, for example those of formulas

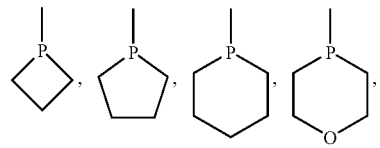

which are unsubstituted or substituted once or more, for example 1, 2, 3, 4, 5 or 6 times, with substituents selected independently of one another from the group consisting of $C_1$-$C_8$ alkyl, $C_4$-$C_8$ cycloalkyl, $C_1$-$C_6$ alkoxy, $C_1$-$C_4$ alkoxy-$C_1$-$C_4$ alkyl, phenyl, $C_1$-$C_4$ alkyl- or $C_1$-$C_4$ alkoxyphenyl, benzyl, $C_1$-$C_4$ alkyl- or $C_1$-$C_4$ alkoxybenzyl, benzyloxy, $C_1$-$C_4$ alkyl- or $C_1$-$C_4$ alkoxybenzyloxy, or $C_1$-$C_4$ alkylidenedioxyl.

The substituents may be bound to the P atom at one or both α positions so as to introduce chiral carbon atoms. The substituents in one or both α positions are preferably $C_1$-$C_4$ alkyl or benzyl, for example methyl, ethyl, n- or iso-propyl, benzyl or —$CH_2$—O—$C_1$-$C_4$ alkyl or —$CH_2$—O—$C_6$-$C_{10}$-aryl.

Substituents at the β,γ positions may, for example, be $C_1$-$C_4$ alkyl, $C_1$-$C_4$ alkoxy, benzyloxy, or —O—$CH_2$—O, —O—CH($C_1$-$C_4$ alkyl)-O, and —O—C($C_1$-$C_4$ alkyl$)_2$-O—. Examples are methyl, ethyl, methoxy, ethoxy, —O—CH(methyl)-O, and —O—C(methyl$)_2$-O—.

An aliphatic 5 or 6 ring or benzene may be fused to two adjacent carbon atoms in the radicals of the above formulas. Depending on the type of substitution and the number of substituents, the cyclic phosphine radicals may be C-chiral, P-chiral or C- and P-chiral.

The cyclic secondary phosphino may correspond, for example, to the following formulas (only one of the possible diastereomers is given),

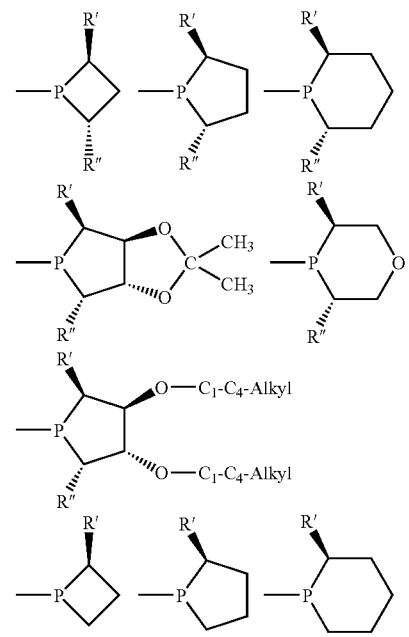

-continued

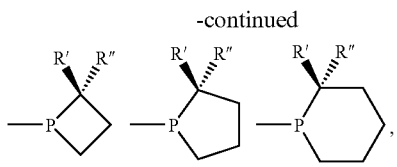

where the radicals R' and R" represent $C_1$-$C_4$ alkyl, for example methyl, ethyl, n- or i-propyl, benzyl, or —$CH_2$—O—$C_1$-$C_4$ alkyl or —$CH_2$—O—$C_6$-$C_{10}$-aryl, and R' and R" are the same or different.

The two secondary phosphino groups —$PR_1R_2$ in diphosphines preferably represent, independently of one another, a non-cyclic secondary phosphine selected from the group of —P($C_1$-$C_6$ alkyl)$_2$, —P($C_5$-$C_8$ cycloalkyl)$_2$, —P($C_7$-$C_8$-bicycloalkyl)$_2$, —P(o-furyl)$_2$, —P($C_6H_5$)$_2$, —P[2-($C_1$-$C_6$ alkyl)$C_6H_4$]$_2$, —P[3-($C_1$-$C_6$ alkyl)$C_6H_4$]$_2$, —P[4-($C_1$-$C_6$ alkyl)$C_6H_4$]$_2$, —P[2-($C_1$-$C_6$ alkoxy)$C_6H_4$]$_2$, —P[3-($C_1$-$C_6$ alkoxy)$C_6H_4$]$_2$, —P[4-($C_1$-$C_6$ alkoxy)$C_6H_4$]$_2$, —P[2-(trifluoromethyl)$C_6H_4$]$_2$, —P[3-(trifluoromethyl)$C_6H_4$]$_2$, —P[4-(trifluoromethyl)$C_6H_4$]$_2$, —P[3,5-bis(trifluoromethyl)$C_6H_3$]$_2$, —P[3,5-bis($C_1$-$C_6$ alkyl)$_2C_6H_3$]$_2$, —P[3,5-bis($C_1$-$C_6$ alkoxy)$_2C_6H_3$]$_2$, and —P[3,5-bis($C_1$-$C_6$ alkyl)$_2$-4-($C_1$-$C_6$ alkoxy)$C_6H_2$]$_2$, or cyclic phosphine selected from the group consisting of:

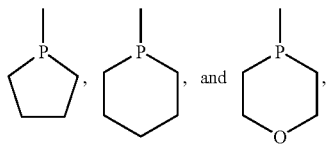

which are unsubstituted or substituted once or more, for example 1, 2, 3, 4, 5 or 6 times, with substituents selected independently of one another from the group consisting of $C_1$-$C_4$ alkyl, $C_1$-$C_4$ alkoxy, $C_1$-$C_4$ alkoxy-$C_1$-$C_2$ alkyl, phenyl, benzyl, benzyloxy, and $C_1$-$C_4$ alkylidene-dioxyl.

Some specific examples are —P($CH_3$)$_2$, —P(iso-$C_3H_7$)$_2$, —P(n-$C_4H_9$)$_2$, —P(iso-$C_4H_9$)$_2$, —P(tert-$C_4H_9$)$_2$, —P($C_5H_9$), —P($C_6H_{11}$)$_2$, —P(norbornyl)$_2$, —P(o-furyl)$_2$, —P($C_6H_5$)$_2$, P[2-(methyl)$C_6H_4$]$_2$, P[3-(methyl)$C_6H_4$]$_2$, —P[4-(methyl)$C_6H_4$]$_2$, —P[2-(methoxy)$C_6H_4$]$_2$, —P[3-(methoxy)$C_6H_4$]$_2$, —P[4-(methoxy)$C_6H_4$]$_2$, —P[3-(trifluoromethyl)$C_6H_4$]$_2$, —P[4-(trifluoromethyl)$C_6H_4$]$_2$, —P[3,5-bis(trifluoromethyl)$C_6H_3$]$_2$, —P[3,5-bis(methyl)$C_6H_3$]$_2$, —P[3,5-bis(methoxy)$_2C_6H_3$]$_2$, —P[3,4,5-trimethoxy$C_6H_2$]$_2$, und —P[3,5-bis(methyl)-4-(methoxy)$C_6H_2$]$_2$, and those of formulas

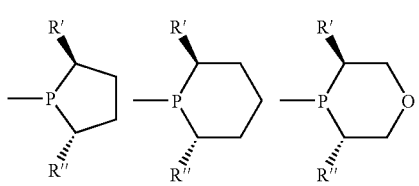

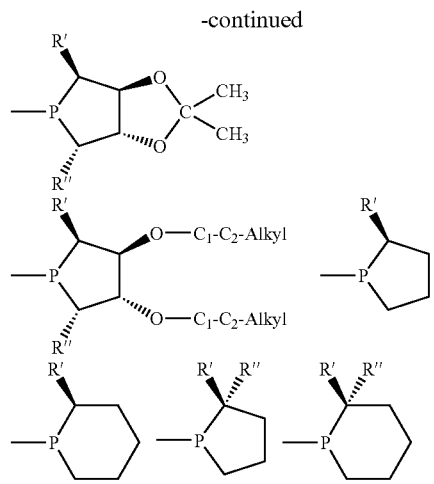

where R' represents methyl, ethyl, methoxy, ethoxy, phenoxy, benzyloxy, methoxy methyl, ethoxy methyl or benzyloxy methyl, and R" is independently the same as R'.

Preferred diphosphine ligands are represented by the following formulas VII to XV:

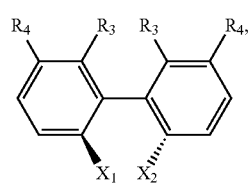

(VII)

where $X_1$ and $X_2$ represent the same or different secondary phosphino, $R_3$ represents $C_1$-$C_4$ alkoxy or $C_1$-$C_4$ alkyl, $R_4$ is hydrogen or is the same as $R_3$, or $R_3$ and $R_4$, together with the carbon atoms to which they are bound, form a five-membered or six-membered carbocyclic ring or a heterocyclic ring with one or more, for example 1 to 4, heteroatoms selected independently of one another from the group O, S, —N= and —N($C_1$-$C_4$ alkyl), for example $R_3$ and $R_4$ possibly representing a radical selected from the group consisting of —CH=CH—CH=CH, —CH=N—CH=CH, —(CH$_2$)$_3$, —(CH$_2$)$_4$, —CH$_2$N($C_1$-$C_4$ alkyl)CH$_2$, —N($C_1$-$C_4$ alkyl)CH$_2$CH$_2$—N($C_1$-$C_4$ alkyl), —O—CH$_2$CH$_2$—N($C_1$-$C_4$ alkyl), —O—CH$_2$CH$_2$—O, —O—CF$_2$—O, —O—CH$_2$—O, —O—CH($C_1$-$C_4$ alkyl)-O, and —O—C($C_1$-$C_4$ alkyl)$_2$-O—;

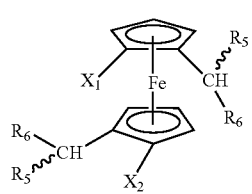

(VIII)

where $X_1$ and $X_2$ represent the same or different secondary phosphino, $R_6$ is a secondary amino, for example —N($C_1$-$C_4$ alkyl)$_2$ and, in particular, dimethylamino, and $R_5$ represents ($C_1$-$C_6$ alkyl), cyclohexyl, phenyl or benzyl;

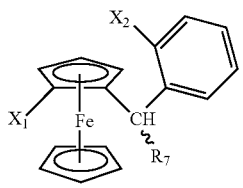 (IX)

where $X_1$ and $X_2$ represent the same or different secondary phosphino and $R_7$ is —OH, $C_1$-$C_{10}$ alkoxy, phenoxy, benzyloxy or $C_1$-$C_8$— alkoxy;

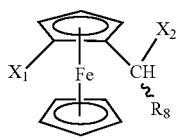 (X)

where $X_1$ and $X_2$ represent the same or different secondary phosphino and $R_8$ is $C_1$-$C_6$ alkyl, cyclohexyl, phenyl or benzyl;

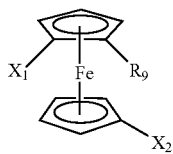 (XI)

where $X_1$ and $X_2$ represent the same or different secondary phosphino and $R_9$ is hydrogen, or represents a —CH($R_7$)$R_8$ group, where $R_7$ is —OH, $C_1$-$C_{10}$ alkoxy, phenoxy, benzyloxy or $C_1$-$C_8$-acyloxy; and $R_8$ is $C_1$-$C_6$ alkyl, cyclohexyl, phenyl or benzyl;

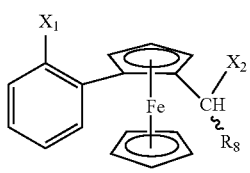 (XII)

where $X_1$ and $X_2$ represent the same or different secondary phosphino and $R_8$ is $C_1$-$C_6$ alkyl, cyclohexyl, phenyl or benzyl;

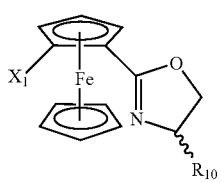 (XIII)

where $X_1$ represents secondary phosphino and $R_{10}$ is $C_1$-$C_6$ alkyl, cyclohexyl, phenyl or benzyl;

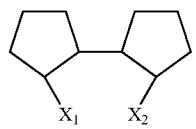 (XIV)

where $X_1$ and $X_2$ represent the same or different secondary phosphino; and P-chiral ethylene-1,2-diphosphines of formula XV

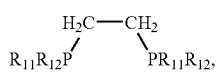 (XV)

where $R_{11}$ and $R_{12}$ represent different hydrocarbon radicals having from 1 to 20 carbon atoms which are unsubstituted or substituted with $C_1$-$C_6$ alkyl and/or $C_1$-$C_6$ alkoxy. A known example is "dipamp" when $R_{11}$ is phenyl and $R_{12}$ is α-methoxyphenyl.

Diphosphine ligands, in particular 1,1'-binaphthyl-6,6'-disecondary phosphines, may be used in ruthenium complexes together with chiral diamines (Noyori method), for example 1,2-diphenyl-ethylene-1,2-diamine (dpen) and 1,1-dibenzyl-2-isopropyl-1,2-diamine (daipen).

The metal complexes of Rh- Ir- Ru-catalysts with chiral diphosphine ligands may contain further ligands and/or anions, depending on the oxidation number and coordination number of the metal. Cationic metal complexes may also be involved. Metal complexes of this type and the production thereof are described numerous times in the literature.

The metal complexes may, for example, correspond to the general formulas XVI and XVII, $$A_1 MeL_n \qquad (XVI),$$

$$(A_1 MeL_n)^{(z+)}(E^-)_z \qquad (XVII),$$

where $A_1$ represents a diphosphine ligand, including the embodiments and preferences, in particular of formulas VII to XV, L represents the same or different monodentates, anionic or non-ionic ligands, or two Ls represent the same or different bidentates, anionic or non-ionic ligands;

n represents 2, 3 or 4 when L is a monodentate ligand, or n represents 1 or 2 when L is a bidentate ligand;

z represents 1, 2 or 3;

Me=rhodium (Rh), iridium (Ir) and ruthenium (Ru), preferably Rh and Ir; in which the metal comprises oxidation states 0, 1, 2, 3 or 4;

$E^-$ is the anion of an oxygen acid or a complex acid; and the anionic ligands compensate for the charge of the oxidation states 1, 2, 3 or 4 of the metal.

Monodentate non-ionic ligands may, for example, be selected from the group of olefins (for example ethylene, propylene), allyls (for example allyl, 2-methallyl), solvating solvents (for example nitriles, linear or cyclic ethers, optionally n alkylated amides and lactams, amines, phosphines (in particular tertiary phosphines, such as triphenyl phosphine), alcohols, carboxylic acid esters, sulfonic acid esters, nitrogen monoxide, carbon monoxide and arenes (for example benzene, mesitylene, cumene).

Monodentate anionic ligands may, for example, be selected from the group of cyclopentadienyl, hydride, halogenide (for example F, Cl, Br, I), pseudohalogenide (for example cyanide, cyanate, isocyanate) and anions of carboxylic acids, sulfonic acids and phosphonic acids (for example carbonate, formate, acetate, propionate, methyl sulfonate, trifluoro methyl sulfonate, phenyl sulfonate, tosylate).

Bidentate non-ionic ligands may, for example, be selected from the group of linear or cyclic diolefins (for example hexadiene, cyclooctadiene, norbornadiene), dinitriles (for example malondinitrile), optionally n alkylated carboxylic acid diamides, diamines, diphosphines, diols, acetonylacetonates, dicarboxylic acid esters and disulfonic acid esters.

Bidentate anionic ligands may, for example, be selected from the group of dicarboxylic acid, disulfonic acid and diphosphonic acid anions (for example oxalic acid, malonic acid, succinic acid, maleic acid, methylene disulfonic acid and methylene diphosphonic acid anions).

Preferred metal complexes are also those in which E represents —Cl' —Br' —I' $ClO_4$' $CF_3SO_3$' $CH_3SO_3$' $HSO_4$' $BF_4$' $B(phenyl)_4$' $B(C_6F_5)_4$' $B(3,5\text{-bistrifluoromethyl-phenyl})_4$' $PF_6$' $SbCl_6$' $AsF_6^-$ or $SbF_6^-$.

Preferred Rh and Ir metal complexes correspond to formulas XVIII and IXX,

[A$_1$Me$_1$YZ]    (XVIII),

[A$_1$Me$_1$Y]$^+$E$_1^-$    (IXX), where
A$_1$ represents a diphosphine ligand, including the embodiments and preferences, in particular of formulas VII to XV;
Me$_1$ is rhodium (Rh) and iridium (Ir);
Y represents two olefins or one diene;
Z is Cl, Br, I or BF$_4^-$; and
E$_1^-$ represents the anion of an oxygen acid or a complex acid.

If Y is olefin, $C_2$-$C_{12}$, preferably $C_2$-$C_6$- and particularly preferably $C_2$-$C_4$-olefins may be involved. Examples are propene, but-1-ene and, in particular, ethylene. The diene may contain from 5 to 12 and preferably from 5 to 8 carbon atoms and may be an open chain, cyclic or polycyclic diene. The two olefin groups of the diene are preferably connected by one or two CH$_2$- groups. Examples are 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene and norbornadiene. Y preferably represents two ethylenes or 1,5-hexadiene, 1,5-cyclooctadiene or norbornadiene.

In formula XVIII, Z preferably represents Cl or Br. Examples of E$_1$ are $ClO_4$' $CF_3SO_3^-$, $CH_3SO_3$' $HSO_4$' $BF_4$'B$(phenyl)_4$' $PF_6$' $SbCl_6$' $AsF_6^-$ or $SbF_6^-$.

Ruthenium complexes may, for example, correspond to formula XX,

[Ru$_a$H$_b$Z$_c$(A$_1$)$_d$L$_e$](E$^k$)$_g$(S)$_h$    (XX), where

Z is Cl, Br or I; A$_1$ represents a diphosphine ligand and preferably a diphoshpine of formulas VII to XV; L represents the same or a different ligand; E$^{k-}$ is the anion of an oxygen acid, mineral acid or complex acid; S represents a solvent which is able to coordinate as a ligand; and a is from 1 to 3, b is from 0 to 4, c is from 0 to 6, d is from 1 to 3, e is from 0 to 4, f is from 1 to 3, g is from 1 to 4, h is from 0 to 6 and k is from 1 to 4, the total charge of the complex being neutral.

The preferences listed above for Z, A$_1$, L and E$^-$ also apply to the compounds of formula XX. The ligands L may also be arenes or heteroarenes (for example benzene, naphthalene, methylbenzene, xylene, cumene, 1,3,5-mesitylene, pyridine, biphenyl, pyrrole, benzimidazole or cyclopentadienyl) and metal salts with a Lewis acid function (for example ZnCl$_2$, AlCl$_3$, TiCl$_4$ and SnCl$_4$). The solvent ligands may be alcohols, amines, acid amides, lactams and sulfones, for example.

Complexes of this type are known and are described in the following literature, as well as in the literature mentioned therein:

D. J. Ager, S. A. Laneman, Tetrahedron: Asymmetry, 8, 1997, 3327-3355;
T. Ohkuma, R. Noyori in Comprehensive Asymmetric Catalysis (E. N. Jacobsen, A. Pfaltz, H. Yamamoto, Eds.), Springer, Berlin, 1999, 199-246;
J. M. Brown in Comprehensive Asymmetric Catalysis (E. N. Jacobsen, A. Pfaltz, H. Yamamoto, Eds.), Springer, Berlin, 1999, 122-182;
T. Ohkuma, M. Kitamura, R. Noyori in Catalytic Asymmetric Synthesis, 2$^{nd}$ Edition (I. Ojima, Ed.), Wiley-VCH New York, 2000, 1-110;
N. Zanetti, et al. Organometallics 15, 1996, 860.

The metal complexes are produced by methods known from the literature (see, for example, Comprehensive Asymmetric Catalysis I bis II, Springer Edition, Berlin, 1999, and literature mentioned therein).

In a particularly preferred embodiment of the process according to the invention, ruthenium complexes are used as homogeneous and chiral hydrogenating catalysts, particularly outstanding results being achieved with those of the [Ru halogenide$_2$(diphosphine formula VII)(chiral diamine)] type and of the [Ru halogenide$_2$(ligand of formula XIII)(tertiary phosphine)] type with regard to selectivity, reaction time (activity), complete conversion and the formation of extremely small amounts of by-products. The halogenide is preferably Cl, Br and I.

It may be advantageous for homogeneous hydrogenation to be carried out in the presence of additives. The amount may reach equimolar amounts or more, based on the compounds of formulas I and II. Examples include acids, inorganic bases (for example NaOH) and alkali metal alcoholates (for example potassium-t-butylate).

It may be particularly advantageous, for example if the substrate is used as a free base, for hydrogenation to be carried out in the presence of acids, for example organic acids such as sulfonic acids (for example methane sulfonic acid, trifluoromethane acid), carboxylic acids (for example formic acid, ethanoic acid, oxalic acid), phosphonic acids (for example methanephosphonic acid), mineral acids such as halogen hydrogen acids (for example HCl, HBr, HI), sulfuric acid, phosphorous acid, phosphoric acid (see, for example, U.S. Pat. Nos. 5,371,256, 5,446,844 and 5,583,241 and EP-A-0 691 949). The acids may be selected in such a way that a desired salt of the active ingredient is directly obtained. Correspondingly, the amount of acids may be up to 1 equivalent or more, for example an excess of up to 1.5 equivalent, based on the amount of substrate to be hydrogenated. A suitable range for the amount is from 0.01 to 1 acid equivalent, based on the amount of substrate to be hydrogenated.

The metal complexes used as catalysts may be added as separately produced, isolated compounds, or may preferably also be formed in situ before the reaction and then mixed with the substrate to be hydrogenated. It may be advantageous to also add ligands during the reaction using isolated metal complexes, or to use an excess of ligands during production in situ. The excess may, for example, be between 1 and 10 and preferably between 1 and 5 mole percent, based on the metal compound used for production.

The process according to the invention is generally carried out in such a way that the catalyst is first introduced, then the substrate, optionally reaction auxiliaries and the gaseous compound to be added in the form of hydrogen are preferably added under pressure. The process may be carried out in various types of reactor either continuously or discontinuously.

According to the invention the alkali metal trialkyl borohydrides and the alkali metal trialkyl aluminium hydrides used may, in particular, correspond to formulas XXI and XXIa,

alkali metal[B(R$_{13}$)$_3$H]　　　　　　　　(XXI),

alkali metal[Al(R$_{13}$)$_3$H]　　　　　　　　(XXIa), where alkali metal represents Li, Na or K and R$_{13}$ is a linear or branched alkyl radical having from 1 to 18, preferably 3 to 18, more preferably 4 to 12 and particularly preferably 4 to 8 carbon atoms. When R$_{13}$ is a branched alkyl, it may comprise at least one asymmetric carbon atom, but this is not as decisive as the influence of steric stress on selectivity.

R$_{13}$ is, for example, preferably branched at the α position. R$_{13}$ may, however, also be branched at the β, γ and/or δ positions. Examples are but-2-yl, pent-2-yl, hex-2-yl, hept-2-yl, oct-2-yl, 2- and 1,2-dimethyl-but-1-yl, 2-ethyl-pent-1-yl, hex-2-yl, 2-methyl- or 2-ethyl-hex-1-yl, 1,2,2-trimethyl-eth-1-yl and 1,2-dimethyl-but-1-yl.

Some compounds of formulas XXI and XXIa are commercially available, for example under the name Selectride®, or can be produced in a similar manner by known methods. Stereoselectivity is particularly high and the ratio of diastereomers of formulas III and IV to diastereomers of formulas V and VI may be >99.5:<0.5. Reactivity is high and complete conversion may be achieved with short reaction times. The formation of by-products may, in particular at temperatures of −20° C. and below, be effectively avoided with amounts of from approximately 1 to less than 10% by weight, based on the reaction product. It may be effective to observe the progress of the reaction and to determine the end of the reaction so as to avoid unnecessarily long reaction times, during which the product may decompose. Ethers, such as diethyl ether, diisopropyl ether, dibutyl ether, ethylene glycol dimethyl ether, dioxane and tetrahydrofuran are particularly suitable as solvents (reaction media).

The following examples illustrate the invention in greater detail without limiting it in any way.

EXAMPLES

The starting product in the form of the racemate of (3R,4R)-4-dimethylaminomethyl-3-hydroxy-3-(3-methoxyphenyl)-cyclohexanone and (3S,4S)-4-dimethylaminomethyl-3-hydroxy-3-(3-methoxyphenyl)-cyclohexanone (compounds of formulas I and II, in which R represents CH$_3$) is referred to hereinafter as cis-1. The production is disclosed, for example in EP-A1-0 753 506 (Example 18). Cis-1 may be separated by known separation methods, such as fractional crystallisation or chromatographic separation of the other stereoisomers (3R,4S)-4-dimethylaminomethyl-3-hydroxy-3-(3-methoxyphenyl)-cyclohexanone and (3S,4R)-4-dimethylaminomethyl-3-hydroxy-3-(3-methoxyphenyl)-cyclohexanone.

The reaction mixture obtained according to the respective example was examined by means of high pressure liquid chromatography (HPLC) with a Nucleosil C8, 25×4.6 mm, 5 μm column at room temperature. Two mobile phases were used: A) acetonitrile/water/0.5M KH$_2$PO$_4$ aq.=5/90/5; and B) acetonitrile/water/0.5M KH$_2$PO$_4$ aq.=60/35/5, and with the following gradients (volume percents): 0 minutes/90% A/10% B; 50 minutes/100% B; 55 minutes 100% B; 56 minutes 90% A/10% B. The flow was 20 μl and detection was carried out at 200 nm. The products were eluted in the following sequence: after 12.5 minutes diastereomers of formulas V and VI, after 14.9 minutes the compounds of formulas I and II (cis-1) and after 18.5 minutes diastereomers of formulas III and IV (desired product).

The ratio of diastereomers of formulas III and IV to diastereomers of formulas V and VI is referred to as selectivity. The following percentage by weight of the catalysts are each based on the amount of cis-1 used.

A) Heterogeneous Hydrogenation

Example A1

Hydrogenation with PtO$_2$ 500 mg (1.8 mmol) cis-1 and 5 ml ethanol were placed in a glass flask together with 1.1 equivalent glacial acetic acid and 15 mg PtO$_2$ (3% by weight) and the glass flask was sealed. The flask was then rinsed in four cycles with argon and in four cycles with hydrogen. 1.1×10$^5$ Pa hydrogen were added under pressure and the reaction was started by activating the stirrer. The mixture was stirred for 24 hours at room temperature, and then the glass flask was rinsed with argon and the catalyst was filtered out. The filtrate was examined by chromatography. Conversion was 91% and selectivity was 93:7.

When the concentration of catalyst was increased to 10% by weight, complete conversion and selectivity of 95:5 were obtained under otherwise identical conditions.

Example A2

Hydrogenation with Raney Nickel 200 mg (0,72 mmol) cis-1, 2 ml solvent and Raney nickel wetted with water (RaNi; type H467, Engelhard, now BASF) were placed in a glass flask which was, in turn, placed in an autoclave and the autoclave was closed. The autoclave was then rinsed in four cycles with argon and in four cycles with hydrogen. Hydrogen was added under pressure and the reaction was started by activating the stirrer. The mixture was stirred at least until the end of the reaction, the glass flask was rinsed with argon and the catalyst was then filtered out. The filtrate was examined chromatographically. Details regarding conversion can be found in Table 1 below together with the results:

The amount of RaNi is given in % by weight (w/w-%) (calculated as a catalyst wetted with water, water content approx. 50% by weight). The temperature (T), when not room temperature (RT), is given in ° C. Hydrogen pressure is given in 10$^5$ Pa. Reaction time is given in hours. The percentage values for cis-1, diastereomers of formulas III and IV (III/IV), diastereomers of formulas V and VI (V/VI) and SAB (sum of all by-products) are by chromatography determined surface percentages. MeOH is methanol, EtOH is ethanol. EtAc is ethyl acetate, iPrOH is isopropanol. Tol is toluene.

TABLE 1

| Amount of RaNi | Solvent | T | Pressure | Time | cis-1 (%) | III/IV (%) | V/VI (%) | SAB (%) | Selectivity |
|---|---|---|---|---|---|---|---|---|---|
| 40 | MeOH | RT | 5 | 17.3 | 0 | 96 | 4 | 0 | 96:4 |
| 40 | MeOH | RT | 50 | 40.3 | 0 | 95 | 4 | 1 | 96:4 |
| 40 | EtOH | RT | 6 | 24 | 0 | 95 | 3 | 2 | 97:3 |
| 20 | EtOH | RT | 6 | 24 | 14 | 78 | 3 | 5 | 96:4 |
| 10 | EtOH | RT | 6 | 24 | 37 | 55 | 2 | 6 | 96:4 |
| 5 | EtOH | RT | 6 | 24 | 55 | 36 | 1 | 8 | 97:3 |
| 40 | EtAc | RT | 6 | 24 | 3 | 87 | 9 | 1 | 91:9 |
| 20 | iPrOH | RT | 6 | 24 | 13 | 80 | 3 | 4 | 96:4 |
| 20 | Tol | RT | 6 | 24 | 4 | 90 | 4 | 2 | 96:4 |
| 20 | Tol | RT | 10 | 6.6 | 55 | 39 | 2 | 4 | 95:5 |
| 20 | Tol | RT | 10 | 23.3 | 29 | 62 | 3 | 7 | 95:5 |
| 40 | Tol | RT | 5 | 4.8 | 66 | 25 | 1 | 8 | 96:4 |
| 40 | Tol | RT | 5 | 27.2 | 2 | 85 | 3 | 10 | 97:3 |
| 20[a] | Tol | RT | 20 | 24 | 76 | 8 | 0 | 16 | 100:0 |
| 20[a] | Tol | 60 | 20 | 24 | 8 | 79 | 3 | 10 | 96:4 |
| 20[a] | Tol | 0 | 20 | 24 | 79 | 8 | 0 | 13 | 100:0 |
| 20[a] | Tol | 60 | 5 | 24 | 64 | 16 | 1 | 19 | 94:6 |
| 40[b] | Tol | RT | 5 | 24 | 36 | 61 | 2 | 1 | 97:3 |
| 40[b] | Tol | RT | 5 | 24 | 37 | 60 | 2 | 1 | 97:3 |
| 40[b],[c] | EtOH | RT | 5 | 24 | 3 | 92 | 2 | 3 | 98:2 |

[a]cis-1 already contained decomposition products (brown color)
[b]cis-1 was recrystallized before hydrogenation from diisopropylether
[c]Variation of Example A2: 50 ml steel autoclave, 2 g (7.2 mmol) cis-1 and 20 ml solvent Example A3

Hydrogenation with Raney Nickel

The process of Example A2 was repeated with 40% by weight RaNi (water content approx. 50% by weight) and the reaction parameters were thus varied. It was found that a higher temperature marginally lowered selectivity and catalyst activity was only slightly affected. At higher pressure, shorter reaction times can be obtained, selectivity remaining practically unchanged. The addition of additives (for example 0.5 equivalent $MgCl_2$, 1.5 equivalent glacial acetic acid or 50% by weight NaOH, based in each case on the cis-1 used) led to a considerable increase of by-products in the reaction mixture. Details are given in Table 2.

TABLE 2

| T | Pressure | Time | cis-1 (%) | III/IV (%) | V/VI (%) | SAB (%) | Selectivity |
|---|---|---|---|---|---|---|---|
| RT | 5 | 24 | 3 | 92 | 2 | 3 | 98:2 |
| 60 | 5 | 28 | 0 | 91 | 5 | 4 | 95:5 |
| 40 | 5 | 27 | 0 | 94 | 4 | 2 | 96:4 |
| 40 | 10 | 24 | 0 | 90 | 6 | 4 | 94:6 |
| 40 | 20 | 24 | 0 | 89 | 3 | 8 | 96:4 |
| 40 | 1.1 | 24 | 17 | 70 | 3 | 10 | 96:4 |
| 40[a] | 5 | 24 | 7 | 64 | 3 | 26 | 96:4 |
| 40 | 5 | 24 | 0 | 89 | 3 | 8 | 96:4 |
| 40[b] | 5 | 24 | 0 | 9 | <1 | 90 | 98:2 |
| 40[c] | 5 | 21 | 0 | 27 | 0 | 73 | 100:0 |

[a]Addition of 0.5 equivalent $MgCl_2$,
[b]1.5 equivalent glacial acetic acid or
[c]50% by weight NaOH. In the last 4 tests cis-1 already contained decomposition products (brown color).

Example A4

Hydrogenation with Raney Nickel

Example A2 was repeated with 40% by weight of various types of catalyst from Engelhard and Degussa wetted in ethanol at 40° C. and $5\times10^5$ Pa. Reaction time was 24 hours. The influence of the type of catalyst on the result was small. The starting product contained approximately 6% by-products. Details are given in Table 3 below.

TABLE 3

| Type of RaNi | cis-1 (%) | III/IV (%) | V/VI (%) | SAB (%) | Selectivity |
|---|---|---|---|---|---|
| EtOH-RaNi H467 | 0 | 89 | 3 | 8 | 96:4 |
| RaNi B111W | 0 | 85 | 6 | 9 | 93:7 |
| RaNi Actimet M | 0 | 88 | 4 | 8 | 95:5 |
| RaNi B113W | 0 | 87 | 7 | 6 | 92:8 |
| RaNi BLM 112 W | 0 | 86 | 6 | 8 | 93:7 |
| RaNi BP 113EXP-B | 0 | 87 | 7 | 6 | 92:8 |
| RaNi Actimet M (washed with EtOH) | 0 | 91 | 6 | 3 | 94:6 |

Example A5

Hydrogenation with Raney Nickel and Reuse of the Catalyst 3.0 g (10.8 mmol) cis-1 suspended in 80 ml ethanol were placed in a 300 ml steel autoclave with a sintered filter plate. 1.2 g Raney nickel (RaNi; type H467, Engelhard, suspended in 20 ml ethanol) wetted with ethanol were then added and the autoclave was closed. The autoclave was then rinsed in three cycles with argon and in three cycles with hydrogen. Hydrogen was added under pressure ($4\times10^5$ Pa) and the reaction was started by activating the stirrer. The mixture was stirred for 24 hours, rinsed with nitrogen and the catalyst was then filtered out and washed with ethanol. The filtrate was examined chormatographically. With the third reuse the catalyst was washed with ethanol, 0.5N NaOH and methanol before it was used again. The starting material cis-1 already contained approximately 25% by-products. Further details and the results can be found in the following Table 4.

TABLE 4

| Comments | Cis-1 (%) | III/IV (%) | V/VI (%) | SAB (%) | Selectivity |
|---|---|---|---|---|---|
| Start of the reaction | 0 | 79 | 5 | 16 | 94:6 |
| First reuse | 6 | 77 | 5 | 12 | 94:6 |
| Second reuse | 23 | 56 | 2 | 19 | 98:2 |
| Third reuse | 0 | 59 | 1 | 40 | 98:2 |

Example A6

Hydrogenation with Raney Nickel and an Increasing Amount of Starting Product Example A2 was repeated and increasing amounts of cis-1 were used. The first 4 tests were carried out in accordance with the variation of Example A2 in a 50 ml steel autoclave. The starting material cis-1 already contained approximately 6% by-products in the first test. Further details can be found in Table 5.

TABLE 5

| mg cis-1/ml | T | Pressure | Time | cis-1 (%) | III/IV (%) | V/VI (%) | SAB (%) | Selectivity |
|---|---|---|---|---|---|---|---|---|
| 100 | 45 | 9 | 23 | 1 | 89 | 3 | 7 | 97:3 |
| 200 | 45 | 9 | 23 | 0 | 94 | 3 | 3 | 97:2 |
| 267 | 45 | 9 | 24 | 0 | 91 | 4 | 5 | 96:4 |
| 333 | 45 | 9 | 24 | 0 | 94 | 4 | 2 | 98:2 |
| 500 | 40 | 5 | 24 | 0 | 95 | 3 | 2 | 97:3 |
| 1000 | 40 | 5 | 24 | 0 | 96 | 3 | 1 | 97:3 |
| 2000 | 40 | 5 | 24 | 26 | 70 | 1 | 3 | 98:2 |

Example A7

Hydrogenation with Raney Nickel with Greater Amounts of the Starting Product Example A5 was repeated with 20 g cis-1 at 40° C. in the presence of 40% by weight RaNi ($H_2O$-H467 or EtOH-H467) in ethanol with a concentration of 1000 mg cis-1 per ml ethanol (tests 1 and 2). The starting material cis-1 contained approximately 2% by-products in tests 1 and 2.

Example A1 was repeated with 50 g cis-1 at 40° C. in the presence of 40% by weight RaNi (Actimet M) in ethanol with a concentration of 1000 mg cis-1 per ml ethanol (test 3). The starting material cis-1 contained approximately 15% by-products in test 3. Before filtration, any undissolved material must be dissolved by adding solvent. The results are summarized in Table 6.

TABLE 6

| Type of RaNi | Pressure | Time | cis-1 (%) | III/IV (%) | V/VI (%) | SAB (%) | Selectivity |
|---|---|---|---|---|---|---|---|
| $H_2O$-H467[a] | 9.5 | 23 | 0 | 88 | 8 | 4 | 92:8 |
| EtOH-H467[a] | 9.5 | 3 | 0 | 87 | 9 | 4 | 91:9 |
| Actimet M[b] | 7 | 2[c] | 2 | 73 | 5 | 20 | 93.7 |

[a] Engelhard,
[b] Degussa,
[c] uptake of hydrogen ended after 30 minutes.

B) Homogeneous Hydrogenation

The ligands used have the following structures:

L1: formula VII, $R_3$ and $R_4$ together are —CH=CH—CH=CH, $X_1$ and $X_2$ are each —P($C_6H_5$)$_2$.
L2: formula XIII, $R_{10}$ is t-butyl, $X_1$ is —P($C_6H_5$)$_2$.
L3: formula XIII, $R_{10}$ is i-propyl, $X_1$ is —P($C_6H_5$)$_2$.
L4: formula XIII, $R_{10}$ is i-propyl, $X_1$ is —P[(3,5-dimethyl-4-methoxy$C_6H_2$)]$_2$.
L5: formula XIII, $R_{10}$ is phenyl, $X_1$ is —P($C_6H_5$)$_2$.
L6: formula VII, $R_3$ and $R_4$ together are —O—$CH_2CH_2$—N($CH_3$), $X_1$ and $X_2$ are each —P[(3,5-dimethyl-$C_6H_3$)]$_2$.
L7: formula VII, $R_3$ and $R_4$ together are —O—$CF_2$—O, $X_1$ and $X_2$ are each —P($C_6H_5$)$_2$.
L8: formula XII, $R_8$ methyl, $X_1$ is —P($C_6H_5$)$_2$, $X_2$ is —P[(3,5-di(trifluoromethyl)-$C_6H_3$)]$_2$ (R,R-configuration).
L9: formula XIV, $X_1$ and $X_2$ are each —P($C_6H_5$)$_2$.
L10: formula X, $R_8$ is methyl, $X_1$ is —P[(3,5-dimethyl-$C_6H_3$)]$_2$, $X_2$ is —P[(3,5-di(trifluoromethyl)-$C_6H_3$)]$_2$.
L11: formula VII, $R_3$ and $R_4$ together are —O—$CH_2CH_2$—N($CH_3$), $X_1$ and $X_2$ are each —P[(3,5-dimethyl-4-methoxy-$C_6H_2$)]$_2$
L12: formula XII, $R_8$ is methyl, $X_1$ is —P[(3,5-dimethyl-4-methyl-$C_6H_2$)]$_2$, $X_2$ is —P[(3,5-di(trifluoromethyl)-$C_6H_3$)]$_2$.
L13: formula VIII, $R_5$ is phenyl and $R_6$ is dimethylamino, $X_1$ and $X_2$ are each —P[(3,5-dimethyl-4-methoxy-$C_6H_2$)]$_2$.
L14: formula XII, $R_8$ methyl, $X_1$ and $X_2$ are each —P($C_6H_5$)$_2$.
L15: formula X, $R_8$ is methyl, $X_1$ is —P($C_6H_5$)$_2$, $X_2$ is —P(t-butyl)$_2$ (S,R-configuration).
L16: formula XII, $R_8$ is methyl, $X_1$ is —P($C_6H_5$)$_2$ and $X_2$ is —P[(3,5-)-di(trifluoromethyl)-$C_6H_3$)]$_2$ (S,R-configuration).
L17: formula IX, $R_7$ is methoxy, $X_1$ and $X_2$ are each —P($C_6H_5$)$_2$.
L18: formula X, $R_8$ is methyl, $X_1$ is —P($C_6H_5$)$_2$, $X_2$ is —P(t-butyl)$_3$ (R,S-configuration).
L19: formula X, $R_8$ is methyl, $X_1$ is —P[(3,5-dimethyl-4-methoxy-$C_6H_2$)]$_2$, $X_2$ is —P[(3,5-di(methyl)-$C_6H_3$)]$_2$.
L20: formula X, $R_8$ is methyl, $X_1$ is —P($C_6H_{11}$)$_2$, $X_2$ is —P(t-butyl)$_2$.
L21: formula IX, $R_7$ is hydroxy, $X_1$ and $X_2$ are each —P($C_6H_5$)$_2$.
L22: formula XV, $R_{11}$ is phenyl, $R_{12}$ is 2-methoxy-phen-1-yl.
L23: formula XII, $R_8$ methyl, $X_1$ is —P(4-methoxy-$C_6H_4$)$_2$, $X_2$ is —P(norbornyl)$_2$.
L24: formula XI, $R_9$ is H, $X_1$ and $X_2$ are each —P(i-propyl)$_2$.
L25: formula X, $R_8$ is methyl, $X_1$ and $X_2$ are each —P[(3,5-di(methyl)-$C_6H_3$)]$_2$.
L26: formula VII, $R_3$ and $R_4$ together are —O—$CH_2CH_2$—N($CH_3$), $X_1$ and $X_2$ are each —P($C_6H_5$)$_2$.

Example B1

Hydrogenation with Ruthenium Complexes

An autoclave was filled with argon at an applied pressure of 10 to 12 bar and unloaded again. This operation was carried out four times. 0.277 g (1.0 mmol) cis-1 was then placed in a 10 ml Schlenk vessel with a magnetic stirrer and then subjected to a sequence of application of a high vaccuum and expanded with argon six times. 5 ml freshly distilled methanol were then added. 60 µl hydrochloric acid (1N) were then carefully added to the solution formed. A metal complex (0.005 mmol) and a ligand (0.0106 mmol) were then added to another 10 ml Schlenk vessel, which was filled with argon by the above method, and dissolved in 5 ml methanol. Both solutions were stirred at room temperature for 10 minutes and then transferred to the autoclaves using cannulae and a light argon flow. The autoclave was filled with hydrogen gas (10 bar, five times) and then hydrogen gas was added under pressure until the desired pressure was reached. The desired reaction temperature was set and stirring was started. After hours of reaction time, the pressure was lowered to normal pressure and the reaction mixture was cooled to room temperature. A clear solution was obtained which was analysed in accordance with the aforementioned chromatographic method. The results are summarized in Table 7.

TABLE 7

| Metal complex | Ligand (configuration) | Additive (ml) | Solution | Pressure $10^6$ Pa | T (° C.) | Conversion (%) | Selectivity |
|---|---|---|---|---|---|---|---|
| [RuCl$_2$(S,S-dpen)] | L1 | 0.3[a] | iPrOH | 2 | 25 | 100 | >99.5:<0.5 |
| [RuCl$_2$(R-daipen)] | L1 | 0.3[a] | iPrOH | 2 | 25 | 100 | 96.7:3.3 |
| [RuCl$_2$(P(C$_6$H$_5$)$_3$)$_3$] | L2 (S, S) | 0.5[b] | Tol | 5 | 25 | 100 | 92.5:7.5 |
| [RuCl$_2$(P(C$_6$H$_5$)$_3$)$_3$] | L2 (S, S) | 1.0[b] | Tol | 2 | 25 | 100 | 92.5:7.5 |
| [RuCl$_2$(P(C$_6$H$_5$)$_3$)$_3$] | L3 (R, R) | 1.0[b] | Tol | 2 | 25 | 100 | 90:10 |
| [RuCl$_2$(P(C$_6$H$_5$)$_3$)$_3$] | L3 (S, S) | 1.0[b] | Tol | 2 | 25 | 100 | 90:10 |
| [RuCl$_2$(P(C$_6$H$_5$)$_3$)$_3$] | L4 (S, S) | 1.0[b] | Tol | 2 | 25 | >99 | 87:13 |
| [RuCl$_2$(P(C$_6$H$_5$)$_3$)$_3$] | L5 (S, S) | 1.0[b] | Tol | 2 | 25 | >98.5 | 75:25 |
| [RuI$_2$(p-Cumol)]$_2$ | L6 (S) | 0.06[c] | MeOH | 8 | 70 | >93 | 92.5:7.5 |
| [RuI$_2$(p-Cumol)]$_2$ | L7 (R) | — | MeOH | 8 | 70 | >97 | 92:8 |
| [RuI$_2$(p-Cumol)]$_2$ | L8 (R., R) | — | MeOH | 9 | 70 | 20 | 90:10 |
| [RuI$_2$(p-Cumol)]$_2$ | L9 (R, R) | — | MeOH | 9 | 50 | 40 | 89:11 |
| [RuI$_2$(p-Cumol)]$_2$ | L10 (R, S) | — | MeOH | 8 | 60 | 50 | 89:11 |
| [RuI$_2$(p-Cumol)]$_2$ | L6 (R) | 0.06[c] | MeOH | 8 | 70 | 92 | 87.4:12.6 |
| [RuI$_2$(p-Cumol)]$_2$ | L11 | 0.06[c] | MeOH | 8 | 70 | 100 | 87:13 |
| [RuI$_2$(p-Cumol)]$_2$ | L12: (R, R) | — | MeOH | 9 | 50 | 35 | 86:14 |
| [RuI$_2$(p-Cumol)]$_2$ | L13 (R, S) | — | MeOH | 9 | 50 | 48 | 86:14 |
| [RuI$_2$(p-Cumol)]$_2$ | L14 (R, R) | — | MeOH | 9 | 50 | 65 | 86:14 |
| [RuI$_2$(p-Cumol)]$_2$ | L15 (S, R) | — | MeOH | 9 | 60 | 60 | 85:15 |
| [RuI$_2$(p-Cumol)]$_2$ | L16 (S, R) | — | MeOH | 9 | 70 | 80 | 84:16 |
| [RuI$_2$(p-Cumol)]$_2$ | L17 (S, S) | — | MeOH | 8 | 80 | 99 | 83:17 |
| [RuI$_2$(p-Cumol)]$_2$ | L18 (R, S) | — | MeOH | 9 | 60 | 50 | 81:19 |
| [RuI$_2$(p-Cumol)]$_2$ | L19 (R, S) | — | MeOH | 8 | 70 | 80 | 80:20 |

[a]potassium-t-butylate (1M);
[b]NaOH (1N);
[c]hydrochloric acid (1N).

The molar ratio (mol/mol) of cis-1 to the catalyst was 200 (1 mmol cis-1 to 0.005 mmol catalyst (precursor).

Example B2

Hydrogenation with Rhodium Complexes

Hydrogenation with rhodium complexes was carried out by the procedure according to Example B1.

The abbreviations are as follows: nbd=norbornadiene, cod=cyclooctadiene. The additive methane sulfonic acid (MsOH) was added in an amount of 0.5 equivalent per equivalent of cis-1. The results are shown in Table 8.

TABLE 8

| Metal complex | Ligand (configuration) | Additive (ml) | Solution | Pressure $10^6$ Pa | T (° C.) | Conversion (%) | Selectivity |
|---|---|---|---|---|---|---|---|
| [Rh(nbd)$_2$]BF$_4$ | L15 (R, S) | — | MeOH | 9 | 70 | 100 | 89.6:10.4 |
| [Rh(nbd)$_2$]BF$_4$ | L11 (R) | MsOH | MeOH | 9 | 60 | 100 | 82:18 |
| [Rh(nbd)Cl]$_2$ | L20 (R, S) | — | Tol | 9 | 70 | 100 | 82:18 |
| [Rh(nbd)$_2$]BF$_4$ | L21 (S, S) | — | MeOH | 5 | 25 | 68 | 80:20 |
| [Rh(cod)L22]BF$_4$ | L22 (S, S) | — | MeOH | 8 | 50 | 70 | 79:21 |
| [Rh(nbd)$_2$]BF$_4$ | L23 (R) | — | MeOH | 9 | 50 | 93 | 79:21 |
| [Rh(cod)L24]BF$_4$ | L24 | MsOH | MeOH | 5 | 50 | 100 | 73.5:26.5 |

Example B3

Hydrogenation with Iridium Complexes

Hydrogenation with iridium complexes was carried out in accordance with the procedure according to Example B1. The reaction time was 18 hours. The additive methane sulfonic acid (MsOH) was added in an amount of 0.5 equivalent per equivalent of cis-1. The amount of solvent was 10 ml. The results are shown in Table 9.

TABLE 9

| Metal complex | Ligand (configuration) | Additive (ml) | Solution | Pressure $10^6$ Pa | T (° C.) | Conversion (%) | Selectivity |
|---|---|---|---|---|---|---|---|
| [Ir(cod)Cl]$_2$ | L6 (R) | — | EtOH | 5 | 25 | 80 | 83.5:16.5 |
| [Ir(cod)Cl]$_2$ | L25 (R, S) | — | EtOH/Tol[a)] | 5 | 25 | 50 | 83.5:16.5 |
| [Ir(cod)Cl]$_2$ | L26 (R) | MsOH | EtOH | 5 | 25 | 30 | 74.5:25.5 |

[a)] volume ratio 1:1

C) Hydrogenation with Metal Hydrides

Example C1

0.1 g cis-1 (0.36 mmol) was placed in a 10 ml Schlenk flask which was then rendered inert by applying a vacuum and rinsing with argon (three times in total). 1.7 ml filtered tetrahydrofuran (THF) were then added using a molecular sieve. The yellow solution was cooled to the desired temperature. At this temperature, 0.36 ml 1 M solution metal hydride in THF (0.36 mmol) was added over 15 minutes. On completion of the reaction, the mixture was left to heat up to room temperature and the reaction mixture was analysed by chromatography. The results are shown in Table 10. Li- or Na-selectride is lithium- or sodium-tris-secondary butylborohydride. LiBH is lithium-tris-isoamylborohydride.

TABLE 10

| Metal hydride (equivalent) | Solvent | T (° C.) | Time (h) | cis-1 (%) | III/IV (%) | V/VI (%) | SAB (%) | Selectivity |
|---|---|---|---|---|---|---|---|---|
| Li-selectride (1) | THF | −78 | 1 | 0 | 98 | <0.5 | 2 | >99.5:<0.5 |
| Li-selectride (1) | THF | −20 | 1 | 0 | 90 | <0.5 | 10 | >99.5:<0.5 |
| Li-selectride (1) | THF | −12 | 0.17 | 0 | 95 | <0.5 | 5 | >99.5:<0.5 |
| Li-selectride (0.8) | THF | −12 | 0.17 | 2 | 89 | <0.5 | 9 | >99.5:<0.5 |
| Na-selectride (1) | THF | −15 | 1 | 0 | 90 | <0.5 | 10 | >99.5:<0.5 |
| LiBH (1) | THF | −15 | 1 | 0 | 84 | 0 | 16 | >99.5:<0.5 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A process for producing compounds corresponding to formulas III or IV or mixtures thereof:

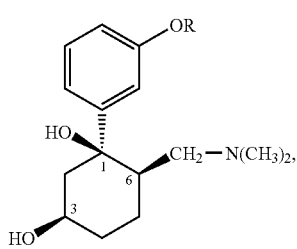

(III)

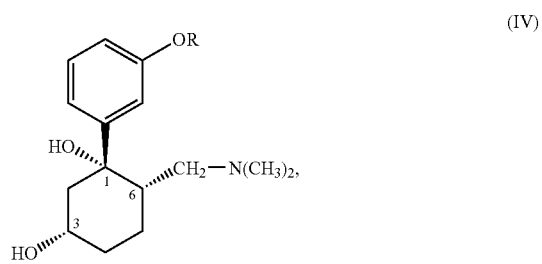

(IV)

wherein R represents hydrogen or $C_1$-$C_4$ alkyl, said process comprising hydrogenating the keto groups of compounds corresponding to formulas I or II or mixtures thereof:

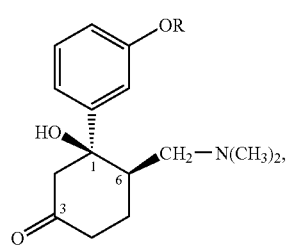

(I)

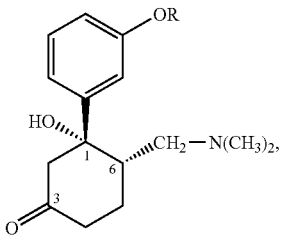

(II)

wherein the hydrogenation is effected:
a) with hydrogen in the presence of platinum dioxide, platinum(IV)chloride, platinum(II)chloride or Raney nickel in the heterogeneous phase; or
b) with hydrogen in the presence of a rhodium, iridium or ruthenium complex with at least one chiral diphosphine ligand, diamine ligand or phosphinite ligand in the homogeneous phase; or
c) with an alkali metal trialkyl borohydride or an alkali metal trialkyl aluminium hydride.

2. A process according to claim 1, wherein R represents hydrogen or methyl.

3. A process according to claim 1, wherein the ratio of diastereomers of formulas III and IV to diastereomers of formulas V and VI

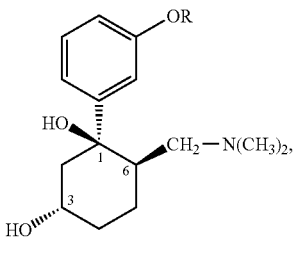

(V)

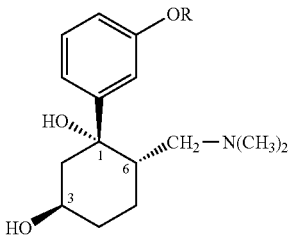

(VI)

is at least 75:25.

4. A process according to claim 1, wherein the hydrogenation is effected in accordance with a) or b) at a hydrogen pressure of from $10^5$ to $2 \times 10^7$ Pascal.

5. A process according to claim 1, wherein the hydrogenation is effected at a temperature of from −80 to 150° C.

6. A process according to claim 1, wherein
the hydrogenation is effected using platinum dioxide in an amount of from 1 to 15% by weight based on the weight of the compounds of formulas I and II, or
the hydrogenation is effected using Raney nickel in an amount of from 1 to 50% by weight based on the weight of the compounds of formulas I and II, or
the hydrogenation is effected using a rhodium, iridium or ruthenium complex with chiral diphosphines in an amount of from 0.0001 to 10% by weight based on the weight of the compounds of formulas I and II, or
the hydrogenation is effected using an alkali metal trialkyl borohydride or alkali metal trialkyl aluminium hydride in an amount of from 0.5 to 1.5 equivalents based on the compounds of formulas I and II.

7. A process according to claim 1, wherein
the hydrogenation is effected using platinum dioxide in an alcohol selected from the group consisting of methanol, ethanol and mixtures thereof, or
the hydrogenation is effected using Raney nickel in an alcohol, carboxylic acid ester, aromatic hydrocarbon or a mixture of two or more thereof.

8. A process according to claim 1, wherein the hydrogenation is effected in the presence of a rhodium, iridium or ruthenium complex with at least one diphosphine ligand corresponding to a secondary phosphino-skeleton-secondary phosphino formula, said ligand forming a five to ten-membered ring with the metal atom and having a skeleton containing from 2 to 30 carbon atoms, and optionally heteroatoms independently selected from the group consisting of O, S, NH and N—$C_1$-$C_4$ alkyl, and optionally transition metal atoms.

9. A process according to claim 8, wherein the skeleton consists of bivalent radicals of alkanes, heteroalkanes, alkenes, cycloalkanes, cycloalkenes, heterocycloalkanes, heterocycloalkenes, bicycloalkanes, bicycloheteroalkanes, spirobiscycloalkanes, spirobiscycloheteroalkanes, arylenes, heteroarylenes, bisarylenes, bisheteroarylenes, metalocenes, and the radicals are unsubstituted or substituted one or more times with substituents selected from the group consisting of $C_1$-$C_6$ alkyl, $C_1$-$C_6$ alkoxy, $C_1$-$C_6$ alkylthio, $C_4$-$C_8$ cycloalkyl, phenyl, benzyl, phenoxy, benzyloxy, phenylthio, benzylthio, halogen, OH, tri($C_1$-$C_6$ alkyl)silyl, secondary amino, —$CO_2H$, —$SO_3H$, —$CO_2R'$, —$SO_3R'$, —O—C(O)—R', —NH—C(O)R', —O—$SO_3$—R' and —NH—$SO_3R'$;
where R' represents $C_1$-$C_6$ alkyl, $C_4$-$C_8$ cycloalkyl, phenyl or benzyl.

10. A process according to claim 9, wherein the skeleton consists of bivalent radicals of ferrocenes.

11. A process according to claim 8, wherein the secondary phosphine groups contain the same or different hydrocarbon radicals as the substituents, and the two secondary phosphine groups in the diphosphine ligand are the same or different.

12. A process according to claim 8, wherein the two secondary phosphino radicals are independently selected from non-cyclic secondary phosphines selected from the group consisting of —P($C_1$-$C_6$ alkyl)$_2$, —P($C_5$-$C_8$ cycloalkyl)$_2$, —P($C_7$-$C_8$-bicycloalkyl)$_2$, —P(o-furyl)$_2$, —P($C_6H_5$)$_2$, —P[2-($C_1$-$C_6$ alkyl)$C_6H_4$]$_2$, —P[3-($C_1$-$C_6$ alkyl)$C_6H_4$]$_2$, —P[4-($C_1$-$C_6$ alkyl)$C_6H_4$]$_2$, —P[2-($C_1$-$C_6$ alkoxy)$C_6H_4$]$_2$, —P[3-($C_1$-$C_6$ alkoxy)$C_6H_4$]$_2$, —P[4-($C_1$-$C_6$ alkoxy)$C_6H_4$]$_2$, —P[2-(trifluoromethyl)$C_6H_4$]$_2$, —P[3-(trifluoromethyl)$C_6H_4$]$_2$, —P[4-(trifluoromethyl)$C_6H_4$]$_2$, —P[3,5-bis(trifluoromethyl)$C_6H_3$]$_2$, —P[3,5-bis($C_1$-$C_6$ alkyl)$_2C_6H_3$]$_2$, —P[3,5-bis($C_1$-$C_6$ alkoxy)$_2C_6H_3$]$_2$, and —P[3,5-bis($C_1$-$C_6$ alkyl)$_2$-4-($C_1$-$C_6$ alkoxy)$C_6H_2$]$_2$; and cyclic phosphines selected from the group consisting of

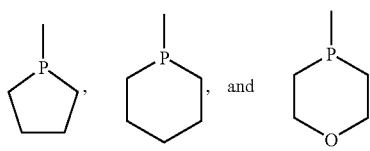

which are each unsubstituted or substituted one or more times with $C_1$-$C_4$ alkyl, $C_1$-$C_4$ alkoxy, $C_1$-$C_4$ alkoxy-$C_1$-$C_2$ alkyl, phenyl, benzyl, benzyloxy, or $C_1$-$C_4$ alkylidene-dioxyl.

13. A process according to claim 8, wherein the diphosphine ligands are selected from the group consisting of ligands corresponding to formulas VII to XV:

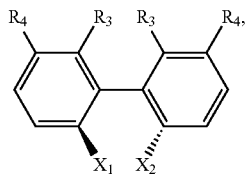
(VII)

where $X_1$ and $X_2$ represent the same or different secondary phosphino, $R_3$ is $C_1$-$C_4$ alkoxy or $C_1$-$C_4$ alkyl, $R_4$ is hydrogen or is the same as $R_3$, or $R_3$ and $R_4$, together with the carbon atoms to which they are bound, form a five or six-membered carbocyclic ring or a heterocyclic ring with heteroatoms independently selected from the group consisting of O, S, —N= and —N($C_1$-$C_4$ alkyl);

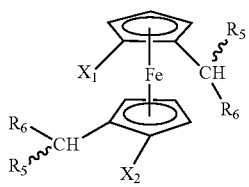
(VIII)

where $X_1$ and $X_2$ represent the same or different secondary phosphino, $R_6$ is secondary amino, and $R_5$ represents ($C_1$-$C_6$ alkyl), cyclohexyl, phenyl or benzyl;

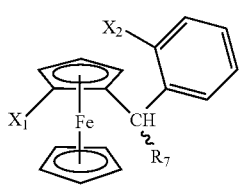
(IX)

where $X_1$ and $X_2$ represent the same or different secondary phosphino, and $R_7$ is —OH, $C_1$-$C_{10}$ alkoxy, phenoxy, benzyloxy or $C_1$-$C_8$-acyloxy;

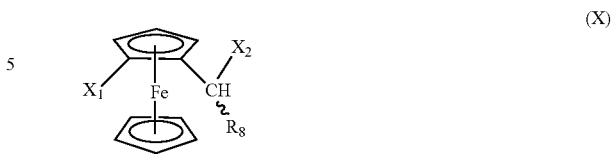
(X)

where $X_1$ and $X_2$ represent the same or different secondary phosphino, and $R_8$ represents $C_1$-$C_6$ alkyl, cyclohexyl, phenyl or benzyl;

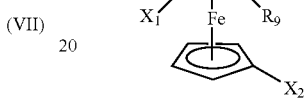
(XI)

where $X_1$ and $X_2$ represent the same or different secondary phosphino, and $R_9$ is hydrogen, or a group —CH($R_7$)$R_8$, where $R_7$ is —OH, $C_1$-$C_{10}$ alkoxy, phenoxy, benzyloxy or $C_1$-$C_8$-acyloxy; and $R_8$ is $C_1$-$C_6$ alkyl, cyclohexyl, phenyl or benzyl;

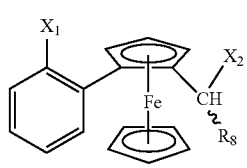
(XII)

where $X_1$ and $X_2$ represent the same or different secondary phosphino, and $R_8$ is $C_1$-$C_6$ alkyl, cyclohexyl, phenyl or benzyl;

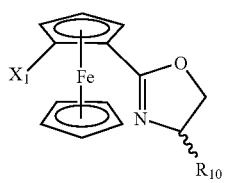
(XIII)

where $X_1$ represents secondary phosphino, and $R_{10}$ is $C_1$-$C_6$ alkyl, cyclohexyl, phenyl or benzyl;

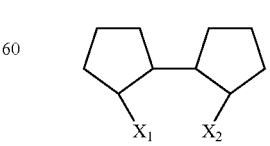
(XIV)

where $X_1$ and $X_2$ represent the same or different secondary phosphino; and

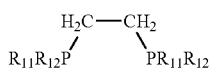

(XV)

where $R_{11}$ and $R_{12}$ represent hydrocarbon radicals having from 1 to 20 carbon atoms which are unsubstituted or substituted with $C_1$-$C_6$ alkyl and/or $C_1$-$C_6$ alkoxy.

14. A process according to claim 13, wherein said ligand is selected from the group consisting of ligands L1 to L26:

L1: formula VII, $R_3$ and $R_4$ together are —CH=CH—CH=CH—, $X_1$ and $X_2$ are each —P($C_6H_5$)$_2$;
L2: formula XIII, $R_{10}$ is tert-butyl, $X_1$ is —P($C_6H_5$)$_2$;
L3: formula XIII, $R_{10}$ is iso-propyl, $X_1$ is —P($C_6H_5$)$_2$;
L4: formula XIII, $R_{10}$ is iso-propyl, $X_1$ is —P[(3,5-dimethyl-4-methoxy$C_6H_2$)]$_2$;
L5: formula XIII, $R_{10}$ is phenyl, $X_1$ is —P($C_6H_5$)$_2$;
L6: formula VII, $R_3$ and $R_4$ together are —O—$CH_2CH_2$—N($CH_3$), $X_1$ and $X_2$ are each —P[(3,5-dimethyl-$C_6H_3$)]$_2$;
L7: formula VII, $R_3$ and $R_4$ together are —O—$CF_2$—O, $X_1$ and $X_2$ are each —P($C_6H_5$)$_2$;
L8: formula XII, $R_8$ is methyl, $X_1$ is —P($C_6H_5$)$_2$, $X_2$ is —P[(3,5-di(trifluoromethyl)-$C_6H_3$)]$_2$ (R,R-configuration);
L9: formula XIV, $X_1$ and $X_2$ are each —P($C_6H_5$)$_2$;
L10: formula X, $R_8$ is methyl, $X_1$ is —P[(3,5-dimethyl-$C_6H_3$)]$_2$, $X_2$ is —P[(3,5-di(trifluoromethyl)-$C_6H_3$)]$_2$;
L11: formula VII, $R_3$ and $R_4$ together are —O—$CH_2CH_2$—N($CH_3$), $X_1$ and $X_2$ are each —P[(3,5-dimethyl-4-methoxy-$C_6H_2$)]$_2$;
L12: formula XII, $R_8$ is methyl, $X_1$ is —P[(3,5-dimethyl-4-methyl-$C_6H_2$)]$_2$, $X_2$ is —P[(3,5-di(trifluormethyl)-$C_6H_3$)]$_2$;
L13: formula VIII, $R_5$ is phenyl and $R_6$ is dimethylamino, $X_1$ and $X_2$ are each —P[(3,5-dimethyl-4-methoxy-$C_6H_2$)]$_2$;
L14: formula XII, $R_8$ is methyl, $X_1$ and $X_2$ are each —P($C_6H_5$)$_2$;
L15: formula X, $R_8$ is methyl, $X_1$ is —P($C_6H_5$)$_2$, $X_2$ is —P(t-butyl)$_2$ (S,R-configuration);
L16: formula XII, $R_8$ is methyl, $X_1$ is —P($C_6H_5$)$_2$ and $X_2$ is —P[(3,5-di(trifluoromethyl)-$C_6H_3$)]$_2$ (S,R-configuration);
L17: formula IX, $R_7$ is methoxy, $X_1$ and $X_2$ are each —P($C_6H_5$)$_2$;
L18: formula X, $R_8$ is methyl, $X_1$ is —P($C_6H_5$)$_2$, $X_2$ is —P(t-butyl)$_3$ (R,S-configuration);
L19: formula X, $R_8$ is methyl, $X_1$ is —P[(3,5-dimethyl-4-methoxy-$C_6H_2$)]$_2$, $X_2$ is —P[(3,5-di(methyl)-$C_6H_3$)]$_2$;
L20: formula X, $R_8$ is methyl, $X_1$ is —P($C_6H_{11}$)$_2$, $X_2$ is —P(t-butyl)$_2$;
L21: formula IX, $R_7$ is hydroxy, $X_1$ and $X_2$ are each —P($C_6H_5$)$_2$;
L22: formula XV, $R_{11}$ is phenyl, $R_{12}$ is 2-methoxy-phen-1-yl;
L23: formula XII, $R_8$ is methyl, $X_1$ is —P(4-methoxy-$C_6H_4$)$_2$, $X_2$ is —P(norbornyl)$_2$;
L24: formula $X_1$, $R_9$ is H, $X_1$ and $X_2$ are each —P(i-propyl)$_2$;
L25: formula X, $R_8$ is methyl, $X_1$ and $X_2$ are each —P[(3,5-di(methyl)-$C_6H_3$)]$_2$; and
L26: formula VII, $R_3$ and $R_4$ together are —O—$CH_2CH_2$—N($CH_3$), $X_1$ and $X_2$ are each —P($C_6H_5$)$_2$.

15. A process according to claim 1, wherein the hydrogenation is effected in the presence of a homogeneous and chiral hydrogenation catalyst comprising:
a [Ru halogenide$_2$(diphosphine of formula VII)(chiral diamine)] complex, or
a [Ru halogenide$_2$(ligand of formula XIII)(tertiary phosphine)] complex.

16. A process according to claim 15, wherein the Ru halogenide$_2$ is formed of Cl, Br or I.

17. A process according to claim 1, wherein the hydrogenation is effected with an alkali metal trialkyl borohydride or alkali metal aluminium hydride corresponding to one of the formulas XXI and XXIa $$\text{alkali metal } [B(R_{13})_3H] \quad (XXI),$$

$$\text{alkali metal}[Al(R_{13})_3H] \quad (XXIa),$$

where alkali metal represents Li, Na or K, and $R_{13}$ is a linear or branched alkyl group containing from 1 to 18 carbon atoms.

18. A process according to claim 17, wherein $R_{13}$ is a linear or branched alkyl group containing from 4 to 12 carbon atoms.

19. A process according to claim 17, wherein the alkyl is branched in the α position.

20. A process according to claim 17, wherein $R_{13}$ is an alkyl group selected from the group consisting of but-2-yl, pent-2-yl, hex-2-yl, hept-2-yl, oct-2-yl, 2-dimethyl-but-1-yl, 1,2-dimethyl-but-1-yl, 2-ethyl-pent-1-yl, 2-methyl-hex-1-yl, 2-ethyl-hex-1-yl, 1,2,2-trimethyl-eth-1-yl, and 1,2-dimethyl-but-1-yl.

* * * * *